(12) United States Patent
Traumer

(10) Patent No.: US 7,131,148 B1
(45) Date of Patent: Nov. 7, 2006

(54) COMBINED BANDANA AND GOGGLES

(76) Inventor: Mark Traumer, 22 Gaffney Pl., Younkers, NY (US) 10704

( * ) Notice: Subject to any disclaimer, the term of this patent is extended or adjusted under 35 U.S.C. 154(b) by 143 days.

(21) Appl. No.: 10/841,660

(22) Filed: May 7, 2004

(51) Int. Cl.
*A61F 9/02* (2006.01)
(52) U.S. Cl. .................... 2/426; 2/10; 2/207; 2/209.13; 2/452
(58) Field of Classification Search .............. 2/10, 2/207, 209.13, 426
See application file for complete search history.

(56) References Cited

U.S. PATENT DOCUMENTS

| | | | |
|---|---|---|---|
| 2,288,423 A | 6/1942 | Root | |
| D144,782 S | 5/1946 | Heinz | |
| 4,176,410 A | 12/1979 | Matthias | |
| 4,520,510 A * | 6/1985 | Daigle | 2/452 |
| 4,682,374 A * | 7/1987 | Geiser | 2/209 |
| 5,421,037 A | 6/1995 | Schulze | |
| 5,461,727 A | 10/1995 | Braswell-Moore | |
| 5,617,589 A | 4/1997 | Lacore et al. | |
| 5,930,842 A * | 8/1999 | Burruss | 2/452 |
| 6,032,292 A * | 3/2000 | Wood et al. | 2/207 |
| 6,047,401 A * | 4/2000 | Traumer | 2/10 |

\* cited by examiner

*Primary Examiner*—Gary L. Welch
*Assistant Examiner*—Alissa J. Tompkins

(57) ABSTRACT

A combined bandana and goggles for protecting a portion of a head of a user from exposure to the elements. The combined bandana and goggles includes a goggles assembly being designed for engaging the head of the user for being positioned over the eyes of the user to inhibit exposure of the eyes to the elements. A cover assembly comprises a head member coupled to a band member. The band member is designed for being secured around the head of the user whereby the head member extends over a top of the head. The band member engages the goggles assembly to maintain positioning of the band member of the head of the user. The head member is designed for inhibiting thermal heat loss through the top of the head and inhibiting contact of the top of the head with the elements.

20 Claims, 4 Drawing Sheets

COMBINED BANDANA AND GOGGLES

BACKGROUND OF THE INVENTION

1. Field of the Invention

The present invention relates to combined goggles and head bands and more particularly pertains to a new combined bandana and goggles for protecting a portion of a head of a user from exposure to the elements.

2. Description of the Prior Art

The use of combined goggles and head bands is known in the prior art. More specifically, combined goggles and head bands heretofore devised and utilized are known to consist basically of familiar, expected and obvious structural configurations, notwithstanding the myriad of designs encompassed by the crowded prior art which have been developed for the fulfillment of countless objectives and requirements.

U.S. Pat. No. 4,520,510 describes a device for being wrapped around the head of the user as a standard headband or as a pair of sunglasses or sunshields. Another type of combined goggles and head band is U.S. Pat. No. 5,461,727 having a cap with an elastic strap around the lower edge of the cap and is selectively coupled to the bridge of pair of glasses to couple the cap to the glasses. U.S. Pat. No. 5,617,589 has a two sided headband that is selectively clipped to the frame of a pair of goggles that are coupled together behind the head of the user to secure the goggles to the head of the user. U.S. Pat. No. 2,288,423 has an eye protector for rider that is positioned over the eyes of a user and has a strap that extends around the head of the user to secure the eye protector over the eyes of the user. U.S. Pat. No. 4,176,410 has a sport goggle that flexes to conform to the face of the user. U.S. Pat. No. 5,421,037 has a headband assembly that fits over a strap of the goggles to provide additionally covering for the ears of a user. U.S. Pat. No. Des. 144,782 shows a pair of goggles.

In these respects, the combined bandana and goggles according to the present invention substantially departs from the conventional concepts and designs of the prior art, and in so doing provides an apparatus primarily developed for the purpose of protecting a portion of a head of a user from exposure to the elements.

SUMMARY OF THE INVENTION

In view of the foregoing disadvantages inherent in the known types of combined goggles and head bands now present in the prior art, the present invention provides a new combined bandana and goggles construction wherein the same can be utilized for protecting a portion of a head of a user from exposure to the elements.

Combined goggles and head bands are known in the prior art, including the inventors prior patent, U.S. Pat. No. 6,047,401, which is hereby and herewith incorporated by reference in its entirety to the extent it is not contradictory with the present invention. While the prior invention disclosed in U.S. Pat. No. 6,047,401 is particularly well suited for its disclosed use, the present invention improves the ability to maintain positioning of the band member of the invention by passing the strap portion of the goggles assembly through the band head and allowing the goggles assembly to keep the band member positioned correctly on the head of the user.

To attain this, the present invention generally comprises a goggles assembly being designed for engaging the head of the user whereby the goggles assembly are for being positioned over the eyes of the user to inhibit exposure of the eyes to the elements while allowing the user to see. A cover assembly comprises a head member and a band member. The the head member is selectively coupled to the band member. The band member is designed for being secured around the head of the user whereby the head member extends over a top of the head of the user. The band member engages the goggles assembly to maintain positioning of the band member on the head of the user. The head member is designed for inhibiting thermal heat loss through the top of the head of the user and inhibiting contact of the top of the head of the user with the elements.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

One significant advantage of the present invention is coverage of the ears and top of the head of the user to protect the ears and top of the head from the elements when the user is participating in an activity such as skiing.

Further advantages of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects of the invention will become apparent when consideration is given to the following detailed description thereof. Such description makes reference to the annexed drawings wherein.

DESCRIPTION OF PREFERRED EMBODIMENTS

Figure 1:
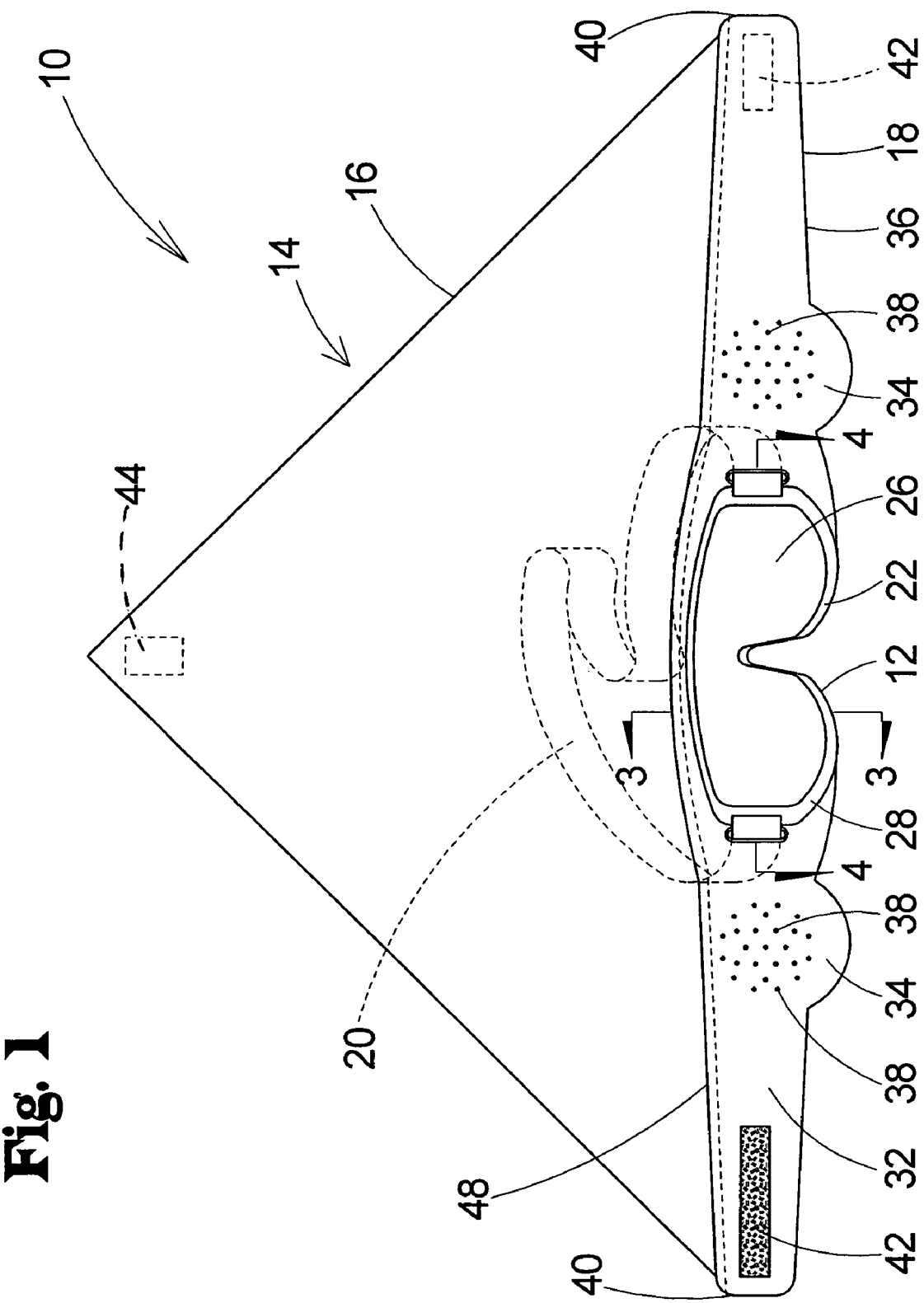
FIG. 1 is a front view of a new combined bandana and goggles according to the present invention.
Figure 2:
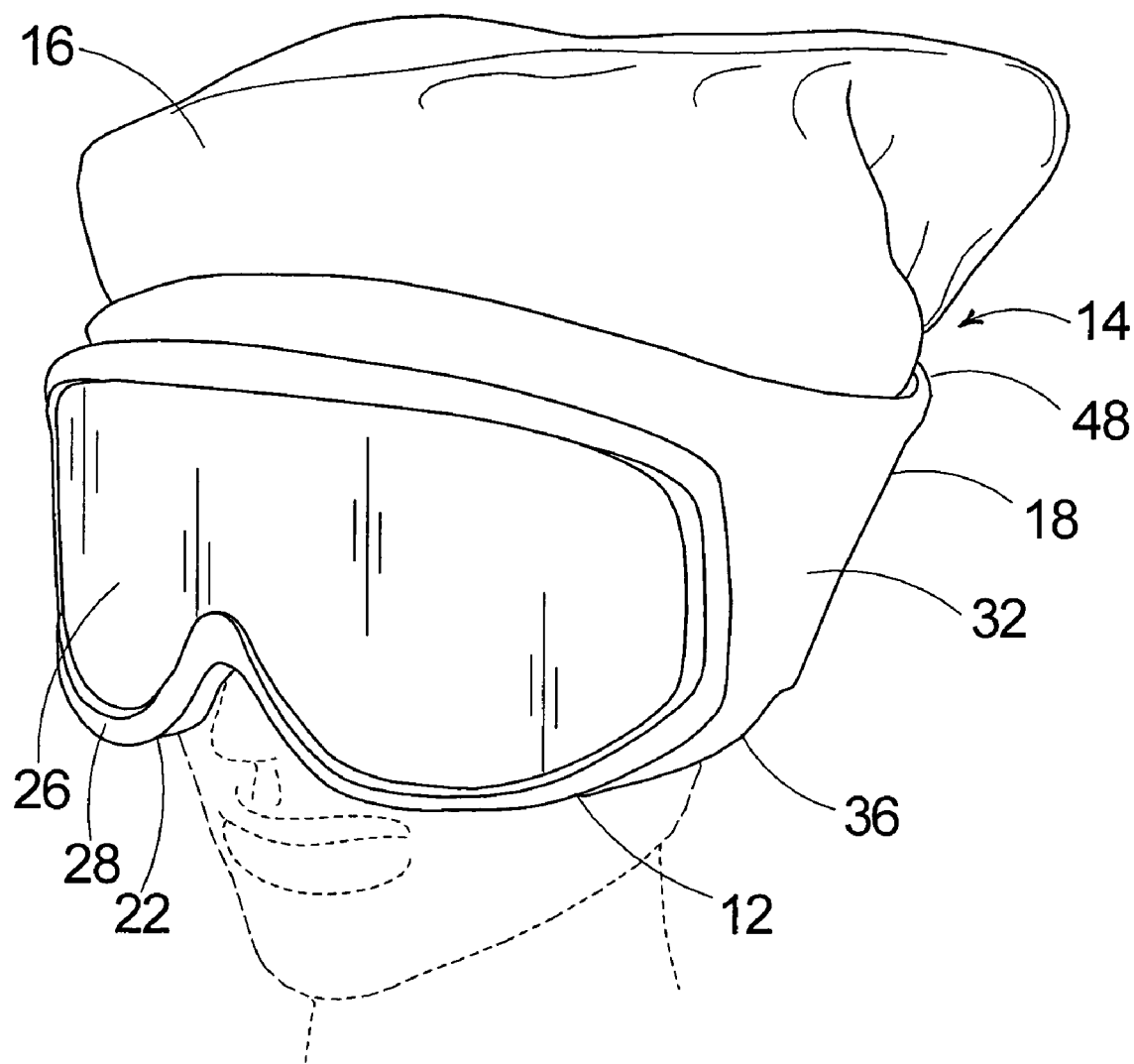
FIG. 2 is a perspective view of the present invention shown in use.
Figure 3:
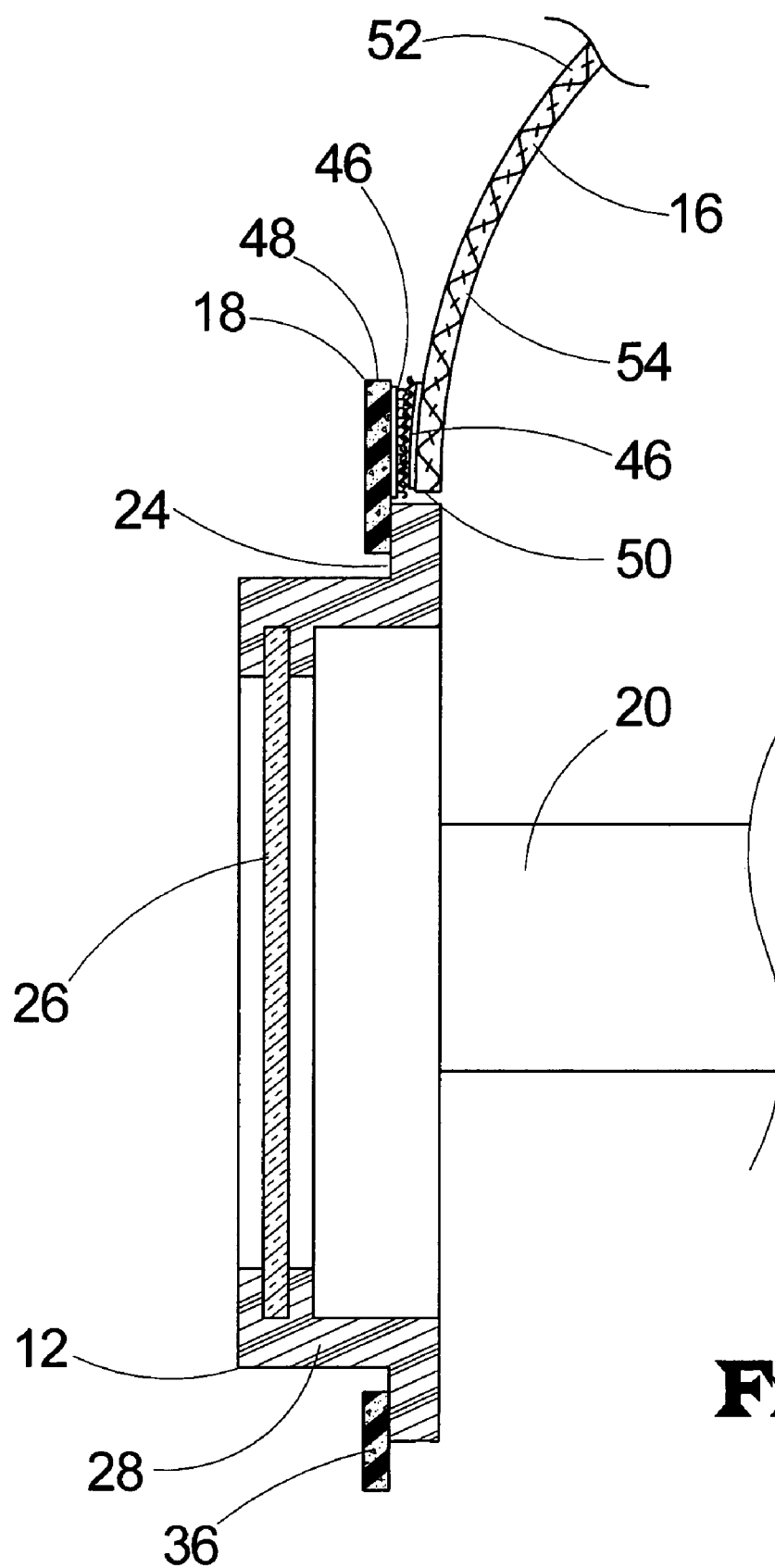
FIG. 3 is a cross-sectional view of the present invention taken along line 3—3 of FIG. 1.
Figure 4:
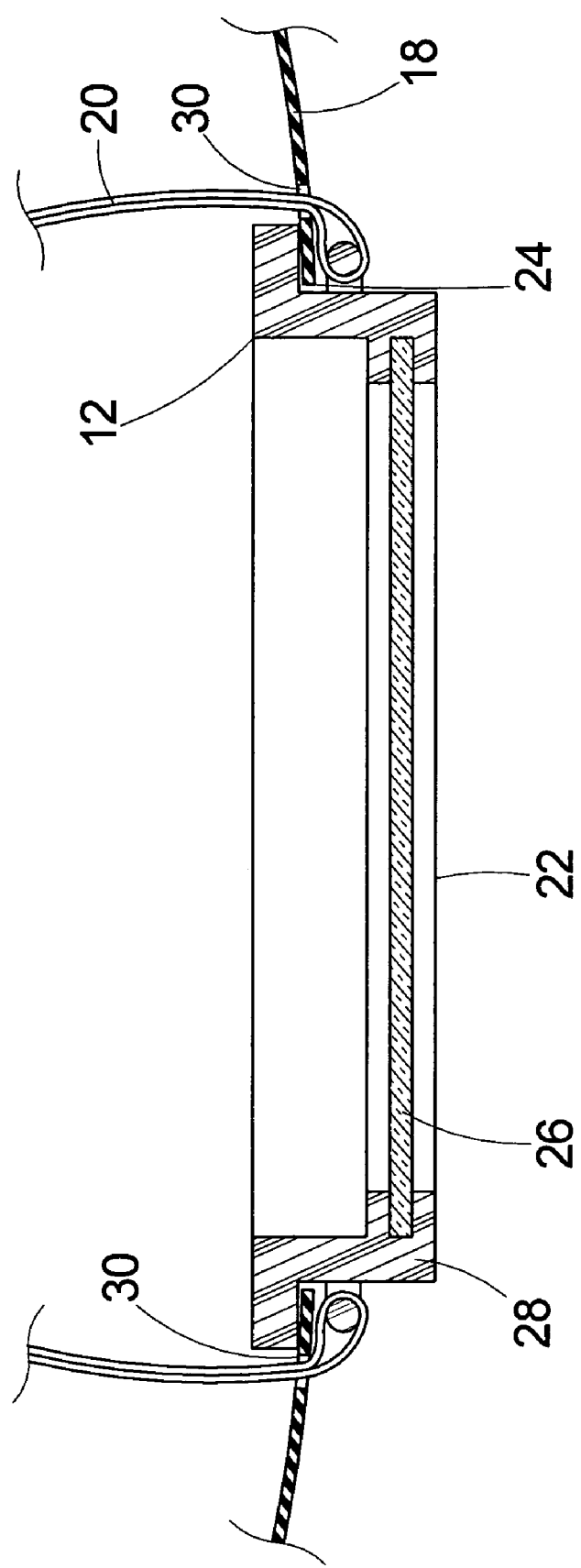
FIG. 4 is a cross-sectional view of the present invention taken along line 4—4 of FIG. 1.

With reference now to the drawings, and in particular to FIGS. 1 through 4 thereof, a new combined bandana and goggles embodying the principles and concepts of the present invention and generally designated by the reference numeral 10 will be described.

As best illustrated in FIGS. 1 through 4, the combined bandana and goggles 10 generally comprises a goggles assembly 12 being designed for engaging the head of the user whereby the goggles assembly 12 are for being positioned over the eyes of the user to inhibit exposure of the eyes to the elements while allowing the user to see.

A cover assembly 14 comprises a head member 16 and a band member 18. The the head member 16 is selectively coupled to the band member 18. The band member 18 is designed for being secured around the head of the user whereby the head member 16 extends over a top of the head of the user. The band member 18 engages the goggles assembly 12 to maintain positioning of the band member 18 on the head of the user. The head member 16 may be substantially triangular in shape. The head member 16 is designed for inhibiting thermal heat loss through the top of the head of the user and inhibiting contact of the top of the head of the user with the elements.

The band member 18 includes a central portion and a pair of end portions. The central portion and each of the end portions have substantially equal lengths. The central portion has a width greater than the width of the end portions.

The goggles assembly 12 comprises a strap portion 20 and a cover portion 22. The strap portion 20 is coupled to the cover portion 22. The strap portion 20 may be continuous between opposite ends that are coupled to the cover portion 22. The cover portion 22 is designed for being positioned over the eyes of the user to inhibit contact between the eyes of the user and the elements. The strap portion 20 is designed for extending around the head of the user to secure the cover portion 22 over the eyes of the user.

The band member 18 comprises a goggles aperture 24 extending through the band member 18. The goggles aperture 24 selectively receives the cover portion 22 of the goggles assembly 12 whereby the band member 18 is positioned around the cover portion 22 of the goggles assembly 12 to maintain positioning of the band member 18 on the head of the user when the cover assembly 14 is positioned on the head of the user and the cover portion 22 of the goggles assembly 12 is positioned over the eyes of the user.

The cover portion 22 of the goggles assembly 12 comprises a lens 26 and a frame 28. The lens 26 is coupled to the frame 28 whereby the frame 28 extends around the lens 26. The frame 28 is selectively positioned in the goggles aperture 24 whereby the band member 18 of the head assembly is positioned around the frame 28 of the cover portion 22 of the goggles member. The frame 28 is designed for abutting a face of the user user whereby the frame 28 is positioned around the eyes of the user. The lens 26 is designed for being positioned over the eyes of the user to inhibit contact between the eyes of the user and the elements when the frame 28 is positioned around the eyes of the user.

The lens 26 of the goggles member comprises a substantially transparent material. The transparent material is designed for permitting the user to see through the lens 26 when the lens 26 is positioned over the eyes of the user.

The band member 18 of the cover assembly 14 comprises a plurality of strap aperture 30s. Each of the strap aperture 30s extends through the band member 18. Each of the strap aperture 30s of the band member 18 selectively receiving a portion of the strap portion 20 of the goggles assembly 12 whereby the strap portion 20 extends through the band member 18. The strap portion 20 of the goggles assembly 12 is designed for being positioned between the head of the user and the band member 18 to permit the cover portion 22 of the goggles assembly 12 to remain positioned over the eyes of the user when the band member 18 is unsecured from the head of the user.

The strap portion 20 of the goggles assembly 12 comprises an elastic material. The elastice materail is designed for conforming and gently compressing against the head of the user to secure the cover portion 22 of the goggles assembly 12 over the eyes of the user.

The band member 18 of the cover assembly 14 comprises a main portion 32 and a pair of extension portions 34. Each of the extension portions 34 is designed for extending downwardly and protruding from a bottom edge 36 of the main portion 32. Each of the extension portions 34 may be semi-circular in shape. Each of the extension portions 34 of the band member 18 is designed for extending over a lower portion of one of the ears of the user when the main portion 32 of the band member 18 is positioned over an upper portion of the ears of the user to inhibit contact between the ears of the user and the elements.

The band member 18 comprises a plurlaity of sound apertures 38. The sound apertures 38 extend through the main portion 32 and the extension portions 34 of the band member 18s. Each of the sound apertures 38 is designed for permitting sound to pass through the band member 18 to permit the user to hear when the ears are covered by the band member 18.

The band member 18 comprises a pair of free ends 40. One of the free ends 40 selectively engages the other one of the free ends 40 to secure the band member 18 around the head of the user. The free ends 40 of the band member 18 are designed for being positioned behind the head of the user when one of the free ends 40 engages the other one of the free ends 40 of the band member 18.

The cover assembly 14 comprises a pair of fastener members 42. Each of the fastener members 42 is coupled to one of the free ends 40 of the band member 18. One of the fastener members 42 is complimentary to the other one of the fastener members 42 for coupling one of the free ends 40 to the other one of the free ends 40 to secure the band member 18 around the head of the user.

The cover assembly 14 comprises a securing member 44. The securing member 44 is coupled to the head member 16 whereby the securing member 44 is positioned opposite the band member 18, such as at an apex of the substantially triangular head member 16. The securing member 44 is complimentary to one of the fastener members 42 whereby the securing member 44 secures the head member 16 to one of the free ends 40 of the band member 18 to secure the head member 16 over the top of the head of the user.

One of the fastener members 42 and the securing member 44 comprise a first portion of hook and loop fastener. The other one of the fastener members 42 comprises a second portion of hook and loop fastener. The first portion of hook and loop fastener of the associated one of the fastener members 42 and the securing member 44 is complimentary to the second portion of hook and loop fastener to secure one of the free ends 40 and the head member 16 to the other one of the free ends 40 of the band member 18.

The cover assembly 14 comprises a pair of coupling members 46. One of the coupling members 46 is coupled to the band member 18 whereby the associated one of the coupling members 46 is positioned adjacent a top edge 48 of the band member 18. The other one of the coupling members 46 is coupled to the head member 16 whereby the associated one of the coupling members 46 is positioned adjacent a perimeter edge 50 of the head member 16. One of the coupling members 46 is complimentary to the other one of the coupling members 46 for selectively coupling the head member 16 to the band member 18.

One of the coupling members 46 comprises a first portion of hook and loop fastener. The other one of the coupling member comprises a second portion of hook and loop fastener. The first portion of hook and loop fastener is complimentary to the second portion of hook and loop fastner to selectively couple the head member 16 to the band member 18.

The band member 18 comprises an elastic insulating material, such as neoprene. The elastic insulating material is designed for conforming to the head of the user and reducing the amount of heat of the user lost through the head when the band member 18 is secured around the head of the user.

The head member 16 of the cover assembly 14 comprises an exterior layer 52 and an interior layer 54. The exterior layer 52 is coupled to the interior layer 54. The exteriror layer is designed for repelling moisture to inhibit the head of the user becoming wet from the elements when the head member 16 is positioned over the top of the head of the user. The interior layer 54 is designed for being positioned against the top of the head of the user whereby the interior layer 54 is for reducing the amount of heat of the user lost through the top of the head when the head member 16 is positioned against the top of the head of the user.

The exterior layer 52 of the head member 16 comprises a moisture proof material. The moisture proof material is designed for permitting moisture to run off of the exterior layer 52 to inhibit the moisture from contacting the head of the user when the head member 16 is positioned over the top of the head of the user.

The interior layer 54 of the head member 16 comprises an insulating material, such as a fleece lining. The insulating material is designed for insulating the top of the head of the user to reduce heat loss through the top of the head of the user when the head member 16 is positioned over the top of the head of the user.

In use, the user extends the strap portion 20 of the goggles assembly 12 through the strap aperture 30s of the band member 18 and the cover portion 22 is positioned in the goggles aperture 24 of the band member 18. The head member 16 is then coupled to the band member 18. The strap portion 20 is positioned around the head and the cover portion 22 is positioned over the eyes of the user. The free ends 40 of the strap member are then positioned around the back of the head of the user. The securing member 44 coupled to the head member 16 is then drawn down and secured to one of the fastener members 42 of one of the free ends 40 of the band member 18 to secure the head member 16 over the top of the head of the user.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A combined bandana and goggles for being worn over eyes and head of a user, the combined bandana and goggles comprising:
    a goggles assembly for engaging the head of the user and positioning over the eyes of the user to inhibit exposure of the eyes to the elements while allowing the user to see; and
    a cover assembly comprising a head member for positioning above the head of the user to inhibit thermal heat loss through the top of the head of the user and inhibiting contact of the top of the head of the user with the elements and a band member for securing around the head of the user, said head member being selectively coupled to said band member such that said head member extends over a top of the head of the user when said band member extends around the head of the user, said band member engaging said goggles assembly to maintain positioning of said band member on the head of the user;
    wherein said goggles assembly comprises a cover portion for being positioned over the eyes of the user to inhibit contact between the eyes of the user and the elements and a strap portion for extending around the head of the user to secure said cover portion over the eyes of the user, said strap portion being coupled to said cover portion.

2. The combined bandana and goggles as set forth in claim 1, wherein said band member comprises a goggles aperture extending through said band member, said goggles aperture receiving said cover portion of said goggles assembly such that said band member is positioned around said cover portion of said goggles assembly to maintain positioning of said band member on the head of the user when said cover assembly is positioned on the head of the user and said cover portion of said goggles assembly is positioned over the eyes of the user.

3. The combined bandana and goggles as set forth in claim 1, wherein said cover portion of said goggles assembly comprises a frame for abutting a face of the user such that said frame is positioned around the eyes of the user and a lens for positioning over the eyes of the user to inhibit contact between the eyes of the user and the elements when said frame is positioned around the eyes of the user, said lens being coupled to said frame such that said frame extends around said lens.

4. The combined bandana and goggles as set forth in claim 3, wherein said lends of said goggle member comprises a substantially transparent material for permitting the user to see through said lens when said lens is positioned over the eyes of the user.

5. The combined bandana and goggles as set forth in claim 1, wherein said band member of said cover assembly comprises a plurality of strap apertures, each of said strap apertures extending through said band member, each of said strap apertures of said band member selectively receiving a portion of said strap portion of said goggles assembly such that said strap portion extends through said band member and is positionable between the head of the user and said band member to permit said cover portion of said goggles assembly to remain positioned over the eyes of the user when said band member is unsecured from the head of the user.

6. The combined bandana and goggles as set forth in claim 1, wherein said strap portion of said goggles assembly comprises an elastic material for conforming and gently compressing against the head of the user to secure said cover portion of said goggles assembly over the eyes of the user.

7. The combined bandana and goggles as set forth in claim 1, wherein said band member of said cover assembly comprises a main portion and a pair of extension portions for extending downwardly from a bottom edge of said main portion for extending over a lower portion of one of the ears of the user when said main portion of said band member is positioned over an upper portion of the ears of the user to inhibit contact between the ears of the user and the elements.

8. The combined bandana and goggles as set forth in claim 7, wherein said band member comprises a plurality of sound apertures for permitting sound to pass through said band member to permit the user to hear when the ears are covered by said band member, said sound apertures extending through said main portion and said extension portions of said band members.

9. The combined bandana and goggles as set forth in claim 1, wherein said band member comprises a pair of free ends for being positioned behind the head of the user when one of said free ends engages the other one of said free ends of said band member, one of said free ends selectively engaging the other one of said free ends to secure said band member around the head of the user.

10. The combined bandana and goggles as set forth in claim 9, wherein said cover assembly comprises a pair of fastener members, each of said fastener members being coupled to one of said free ends of said band member, one of said fastener members being complimentary to the other one of said fastener members for coupling one of said free ends to the other one of said free ends to secure said band member around the head of the user.

11. The combined bandana and goggles as set forth in claim 10, wherein said cover assembly comprises a securing member, said securing member being coupled to said head member such that said securing member is positioned opposite said band member, said securing member being complimentary to one of said fastener members such that said securing member secures said head member to one of said free ends of said band member to secure said head member over the top of the head of the user.

12. The combined bandana and goggles as set forth in claim 11, wherein one of said fastener members and said securing member comprises a first portion of hook and loop fastener, the other one of said fastener members comprising a second portion of hook and loop fastener, said first portion of hook and loop fastener of the associated one of said fastener members and said securing member being complimentary to said second portion of hook and loop fastener to secure one of said free ends and said head member to the other one of said free ends of said band member.

13. The combined bandana and goggles as set forth in claim 1, wherein said cover assembly comprises a pair of coupling members, one of said coupling members being coupled to said band member such that the associated one of said coupling members is positioned adjacent a top edge of said band member, the other one of said coupling members being coupled to said head member such that the associated one of said coupling members is positioned adjacent a perimeter edge of said head member, one of said coupling members being complimentary to the other one of said coupling members for selectively coupling said head member to said band member.

14. The combined bandana and goggles as set forth in claim 13, wherein one of said coupling members comprises a first portion of hook and loop fastener, the other one of said coupling member comprising a second portion of hook and loop fastener, said first portion of hook and loop fastener to selectively couple said head member to said band member.

15. The combined bandana and goggles as set forth in claim 1, wherein said band member comprises an elastic insulating material for conforming to the head of the user and reducing the amount of heat of the user lost through the head when said band member is secured around the head of the user.

16. The combined bandana and goggles as set forth in claim 1, wherein said head member of said cover assembly comprises an exterior layer for repelling moisture to inhibit the head of the user becoming wet from the elements when said head member is positioned over the top of the head of the user and an interior layer for being positioned against the top of the head of the user such that said interior layer is for reducing the amount of heat of the user lost through the top of the head when said head member is positioned against the top of the head of the user, said exterior layer being coupled to said interior layer.

17. The combined bandana and goggles as set forth in claim 16, wherein said exterior layer of said head member comprises a moisture proof material for permitting moisture to run off of said exterior layer to inhibit the moisture for contacting the head of the user when said head member is positioned over the top of the head of the user.

18. The combined bandana and goggles as set forth in claim 16, wherein said interior layer of said head member comprises an insulating material for insulating the top of the head of the user to reduce heat loss through the top of the head of the user when said head member is positioned over the top of the head of the user.

19. The combined bandana and goggles for being worn over eyes and head of a user, the combined bandana and goggles comprising:

a goggles assembly for engaging the head of the user and positioning over the eyes of the user to inhibit exposure of the eyes to the elements while allowing the user to see;

a cover assembly comprising a head member for positioning above the head of the user to inhibit thermal head loss through the top of the head of the user and inhibiting contact of the top of the head of the user with the elements and a band member for securing around the head of the user, said head member being selectively coupled to said band member such that said head member extends over a top of the head of the user when said band member extends around the head of the user, said band member engaging said goggles assembly to maintain positioning of said band member on the head of the user;

said goggles assembly comprising a cover portion for being positioned over the eyes of the user to inhibit contact between the eyes of the user and the elements and a strap portion for extending around the head of the user to secure said cover portion over the eyes of the user, said strap portion being coupled to said cover portion;

said band member comprising a goggles aperture extending through said band member, said goggles aperture receiving said cover portion of said goggles assembly such that said band member is positioned around said cover portion of said goggles assembly to maintain positioning of said band member on the head of the user when said cover assembly is positioned on the head of the user and said cover portion of said goggles assembly is positioned over the eyes of the user;

said cover portion of said goggles assembly comprising a frame for abutting a face of the user such that said frame is positioned around the eyes of the user and a lens for positioning over the eyes of the user to inhibit contact between the eyes of the user and the elements when said frame is positioned around the eyes of the user, said lens being coupled to said frame such that said frame extends around said lens;

said lens of said goggle member comprising a substantially transparent material for permitting the user to see through said lens when said lens is positioned over the eyes of the user;

said band member of said cover assembly comprising a plurality of strap apertures, each of said strap apertures extending through said band member, each of said strap apertures of said band member selectively receiving a portion of said strap portion of said goggles assembly such that said strap portion extends through said band member and is positionable between the head of the user and said band member to permit said cover portion of said goggles assembly to remain positioned over the eyes of the user when said band member is unsecured from the head of the user;

said strap portion of said goggles assembly comprising an elastic material for conforming and gently compressing against the head of the user to secure said cover portion of said goggles assembly over the eyes of the user;

said goggles of said cover assembly comprising a main portion and a pair of extension portions for extending downwardly from a bottom edge of said main portion for extending over a lower portion of use of the ears of the user portion of the ears of the user to inhibit contact between the ears of the user and the elements;

said band member comprising a plurality of sound apertures for permitting sound to pass through said band member to permit the user to hear when the ears are covered by said band member, said sound apertures extending through said main portion and said extension portions of said band members;

said band member comprising a pair of free ends for being positioned behind the head of the user when one of said free ends engages the other one of said free ends of said band member, one of said free ends selectively engaging the other one of said free ends to secure said band member around the head of the user;

said cover assembly comprising a pair of fastener members, each of said fastener members being coupled to one of said free ends of said band member, one of said fastener members being complimentary to the other one of said fastener members for coupling one of said free ends to the other one of said free ends to secure said band member around the head of the user;

said cover assembly comprising a securing member, said securing member being coupled to said head member such that said securing member is positioned opposite said band member, said securing member being complimentary to one of said fastener members such that said securing member secures said head member to one of said free ends of said band member to secure said head member over the top of the head of the user;

one of said fastener members and said securing member comprising a first portion of hook and loop fastener, the other one of said fastener members comprising a second portion of hook and loop fastener, said first portion of hook and loop fastener of the associated one of said fastener members and said securing member being complimentary to said second portion of hook and loop fastener to secure one of said free ends and said head member to the other one of said free ends of said band member;

said cover assembly comprising a pair of coupling members, one of said coupling members being coupled to said band member such that the associated one of said coupling members is positioned adjacent a top edge of said band member, the other one of said coupling members being coupled to said head member such that the associated one of said coupling members is positioned adjacent a perimeter edge of said head member, one of said coupling members being complimentary to the other one of said coupling members for selectively coupling said head member to said band member;

one of said coupling members comprising a first portion of hook and loop fastener, the other one of said coupling member comprising a second portion of hook and loop fastener, said first portion of hook and loop fastener being complimentary to said second portion of hook and loop fastner to selectively couple said head member to said band member;

said band member comprising an elastic insulating material for conforming to the head of the user and reducing the amount of heat of the user lost through the head when said band member is secured around the head of the user;

said head member of said cover assembly comprising an exterior layer for repelling moisture to inhibit the head of the user becoming wet from the elements when said head member is positioned over the top of the user of the user and an interior layer for being positioned against the top of the head of the user such that said interior layer is for reducing the amount of heat of the user lost through the top of the head when said head member is positioned against the top of the head of the user, said exterior layer being coupled to said interior layer;

said exterior layer of said head member comprising a moisture proof material for permitting moisture to run off of said exterior layer to inhibit the moisture from contacting the head of the user when said head member is positioned over the top of the head of the user; and said interior layer of said head member comprising an insulating material for insulating the top of the head of the user to reduce heat loss through the top of the head of the user when said head member is positioned over the top of the head of the user.

20. A bandana and goggles combination for being worn by a user, the bandana and goggles combination comprising:

a goggles assembly for engaging the head of the user and positioning over the eyes of the user, said goggles assembly comprising:
  a cover portion for being positioned over the eyes of the user to inhibit contact between the eyes of the user and the elements; and
  a strap portion for extending around the head of the user to secure said cover portion over the eyes of the user, said strap portion being coupled to said cover portion; and a cover assembly for inhibiting thermal heat loss through the top of the user, said cover assembly comprising:
  a band member for securing around the head of the user, said band member being mounted on the cover portion of said goggles assembly to maintain positioning of said band member on the head of the user; and
  a head covering member for positioning above the head of the user, said head member being selectively coupled to said band member such that said head member is positionable over a top of the head of the user when said band member extends around the head of the user.

* * * * *